(12) United States Patent
Brzezinski et al.

(10) Patent No.: US 10,292,752 B2
(45) Date of Patent: May 21, 2019

(54) ELECTROCAUTERY TACTILE FEEDBACK SYSTEMS AND METHODS

(71) Applicants: Anna Brzezinski, Chicago, IL (US); Katherine J. Kuchenbecker, Philadelphia, PA (US); Ernest D. Gomez, Philadelphia, PA (US); Nicole Blumenfeld, New York, NY (US); Brian H. Horwich, Los Angeles, CA (US); Zachary E. Shurden, Brooklyn, NY (US)

(72) Inventors: Anna Brzezinski, Chicago, IL (US); Katherine J. Kuchenbecker, Philadelphia, PA (US); Ernest D. Gomez, Philadelphia, PA (US); Nicole Blumenfeld, New York, NY (US); Brian H. Horwich, Los Angeles, CA (US); Zachary E. Shurden, Brooklyn, NY (US)

(73) Assignees: Anna Brzezinski, Chicago, IL (US); Katherine J. Kuchenbecker, Philadelphia, PA (US); Ernest D. Gomez, Philadelphia, PA (US); Nicole Blumenfeld, New York, NY (US); Brian H. Horwich, Los Angeles, CA (US); Zachary Shurden, Brooklyn, NY (US)

( * ) Notice: Subject to any disclaimer, the term of this patent is extended or adjusted under 35 U.S.C. 154(b) by 433 days.

(21) Appl. No.: 14/785,464

(22) PCT Filed: Apr. 17, 2014

(86) PCT No.: PCT/US2014/034443
§ 371 (c)(1),
(2) Date: Oct. 19, 2015

(87) PCT Pub. No.: WO2014/172514
PCT Pub. Date: Oct. 23, 2014

(65) Prior Publication Data
US 2016/0081738 A1    Mar. 24, 2016

Related U.S. Application Data

(60) Provisional application No. 61/813,670, filed on Apr. 19, 2013.

(51) Int. Cl.
*A61B 18/12*    (2006.01)
*A61B 17/00*    (2006.01)
*A61B 18/00*    (2006.01)

(52) U.S. Cl.
CPC ..... *A61B 18/1206* (2013.01); *A61B 2017/00973* (2013.01); *A61B 2018/00303* (2013.01); *A61B 2018/00827* (2013.01)

(58) Field of Classification Search
CPC ...... A61B 18/1206; A61B 2017/00973; A61B 2018/00303; A61B 2018/00827
See application file for complete search history.

(56) References Cited

U.S. PATENT DOCUMENTS 3,683,923 A * 8/1972 Anderson ............. A61B 18/16
                                                      128/908
5,339,799 A * 8/1994 Kami ..................... A61B 18/14
                                                      600/109

(Continued)

FOREIGN PATENT DOCUMENTS

WO    1994024949    11/1994

OTHER PUBLICATIONS

Choi, S., et al., "Vibrotactile display: Perception, technology, and applications," Sep. 2013, pp. 2093-2104, vol. 101(9), Proceedings of the IEEE.

(Continued)

*Primary Examiner* — Michael F Peffley
*Assistant Examiner* — Amanda L Zink
(74) *Attorney, Agent, or Firm* — Arent Fox LLP

(57) ABSTRACT

Surgery systems and methods for providing vibration feedback are disclosed. A surgery system includes an electrocautery tool, a current sensor, and an actuator. The current sensor is coupled to the electrocautery tool to sense a current through the electrocautery tool indicative of an electrocautery action being performed with the tool. The actuator is in communication with the current sensor and is configured to provide a vibration to an operator of the electrocautery tool when the current sensor senses the current through the electrocautery tool indicative of the electrocautery action. A surgical method includes sensing a current through an electrocautery tool indicative of an electrocautery action being performed with the tool, and actuating an actuator to provide a vibration to an operator of the electrocautery tool when the current sensor senses the current through the electrocautery tool indicative of the electrocautery action.

5 Claims, 6 Drawing Sheets

(56) References Cited

U.S. PATENT DOCUMENTS

| | | | | |
|---|---|---|---|---|
| 5,688,270 | A * | 11/1997 | Yates | A61B 17/07207 606/41 |
| 5,707,369 | A | 1/1998 | Vaitekunas | |
| 5,713,896 | A * | 2/1998 | Nardella | A61B 17/07207 606/41 |
| 2004/0046777 | A1 * | 3/2004 | Tremblay | G06F 3/011 715/702 |
| 2006/0079872 | A1 | 4/2006 | Eggleston | |
| 2009/0248017 | A1 * | 10/2009 | Heard | A61B 18/1477 606/42 |
| 2010/0228264 | A1 * | 9/2010 | Robinson | A61B 18/1206 606/130 |
| 2011/0015627 | A1 * | 1/2011 | DiNardo | A61B 17/320092 606/34 |
| 2012/0041436 | A1 | 2/2012 | Ullrich | |
| 2012/0143182 | A1 * | 6/2012 | Ullrich | A61B 18/1445 606/45 |
| 2014/0005682 | A1 | 1/2014 | Worrell | |
| 2014/0163549 | A1 | 6/2014 | Yates | |

OTHER PUBLICATIONS

International Preliminary Report on Patentability and Written Opinion for International Application No. PCT/US2014/034443 dated Oct. 20, 2015.

International Search Report for International Application No. PCT/US2014/034443 dated Sep. 23, 2014.

Okamura, A.M., "Haptic feedback in robot-assisted minimally invasive surgery," Jan. 2009, pp. 102-107, vol. 19(1), Current Opinion in Urology.

Precision Microdrives, 2012, 12mm Vibration motor. Retrieved from https://catalog.precisionmicrodrives.com/order-parts/product/312-201-12mm-vibration-motor-20mm-type, pp. 1-5.

Sparkfun Electronics, 2011, Arduino Uno—R3. Retrieved from https://www.sparkfun.com/products/11021, one page.

Sparkfun Electronics, 2012, Wireless Transmitters. Retrieved from https://www.sparkfun.com/categories/79?sort_by=price_asc&per_page=50, pp. 1-3.

* cited by examiner

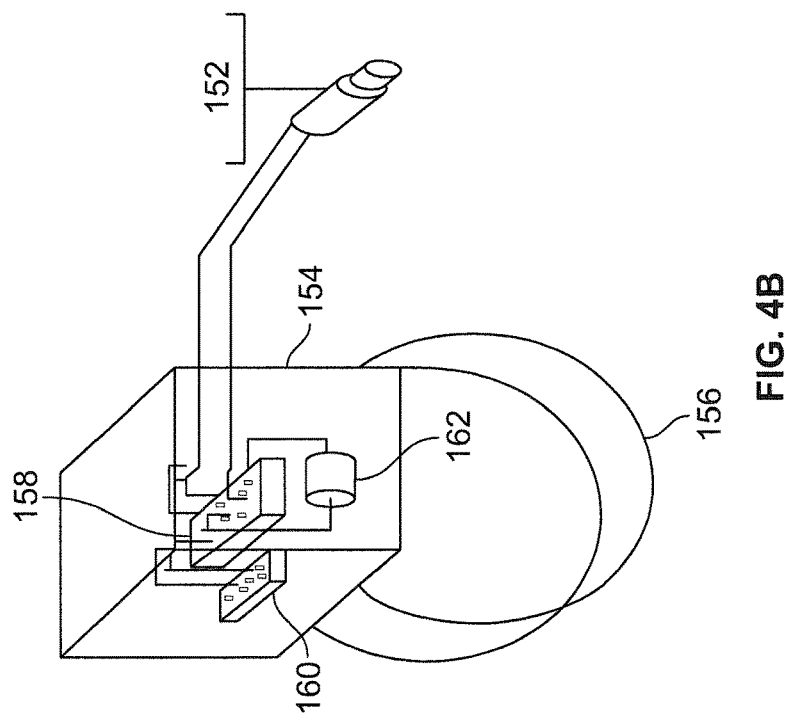
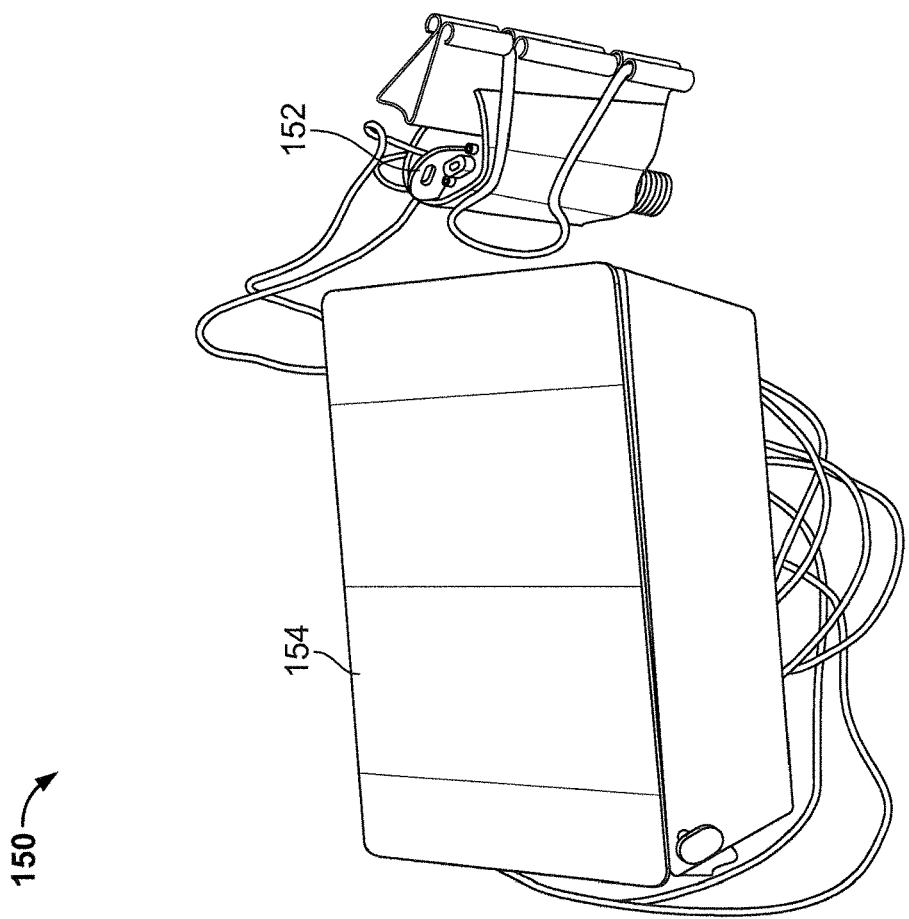

ELECTROCAUTERY TACTILE FEEDBACK SYSTEMS AND METHODS

CROSS-REFERENCE TO RELATED APPLICATIONS

This application claims priority to U.S. Patent Application No. 61/813,670, entitled "ELECTROCAUTERY TACTILE FEEDBACK SYSTEMS AND METHODS," filed Apr. 19, 2013, the contents of which are incorporated herein by reference in their entirety.

This application is a U.S. National Phase of PCT International Application PCT/US2014/034443.

FIELD OF THE INVENTION

The present invention relates generally to surgery systems, and more particularly to providing vibration feedback for users of surgical energy delivery systems.

BACKGROUND OF THE INVENTION

Electrocautery is a surgical technique widely used in surgery whereby electric current is delivered to a patient's tissue for the purposes of dissection or vasculature coagulation. In bipolar electrocautery, current is passed from one metal probe, through the patient's tissue, and returns to the tool through a second metal probe that is in close proximity to the first. Bipolar electrocautery allows for localized energy delivery. In monopolar electrocautery, current flows from a metal probe at the end of the tool handle, radiates outward into the patient's tissue, and returns to the generator through a ground pad usually placed on the patient's leg. Both types of electrocautery are widely used but serve different functions.

SUMMARY OF THE INVENTION

Aspects of the presented invention are directed to surgery systems and methods for providing vibration feedback.

In accordance with one aspect of the present invention, a surgery system is disclosed. The surgery system includes an electrocautery tool, a current sensor, and an actuator. The current sensor is coupled to the electrocautery tool to sense a current through the electrocautery tool indicative of an electrocautery action being performed with the tool. The actuator is in communication with the current sensor and is configured to provide a vibration to an operator of the electrocautery tool when the current sensor senses the current through the electrocautery tool indicative of the electrocautery action.

In accordance with another aspect of the present invention, a method for providing vibration feedback during electrocauterization is disclosed. The method includes sensing a current through an electrocautery tool indicative of an electrocautery action being performed with the tool, and actuating an actuator to provide a vibration to an operator of the electrocautery tool when the current sensor senses the current through the electrocautery tool indicative of the electrocautery action.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. According to common practice, the various features of the drawings are not drawn to scale unless otherwise indicated. To the contrary, the dimensions of the various features may be expanded or reduced for clarity. Included in the drawings are the following figures:

FIGS. 4A and 4B are an image and a diagram illustrating an exemplary feedback device of the surgery system of FIG. 1;

DETAILED DESCRIPTION OF THE INVENTION

Figure 1:
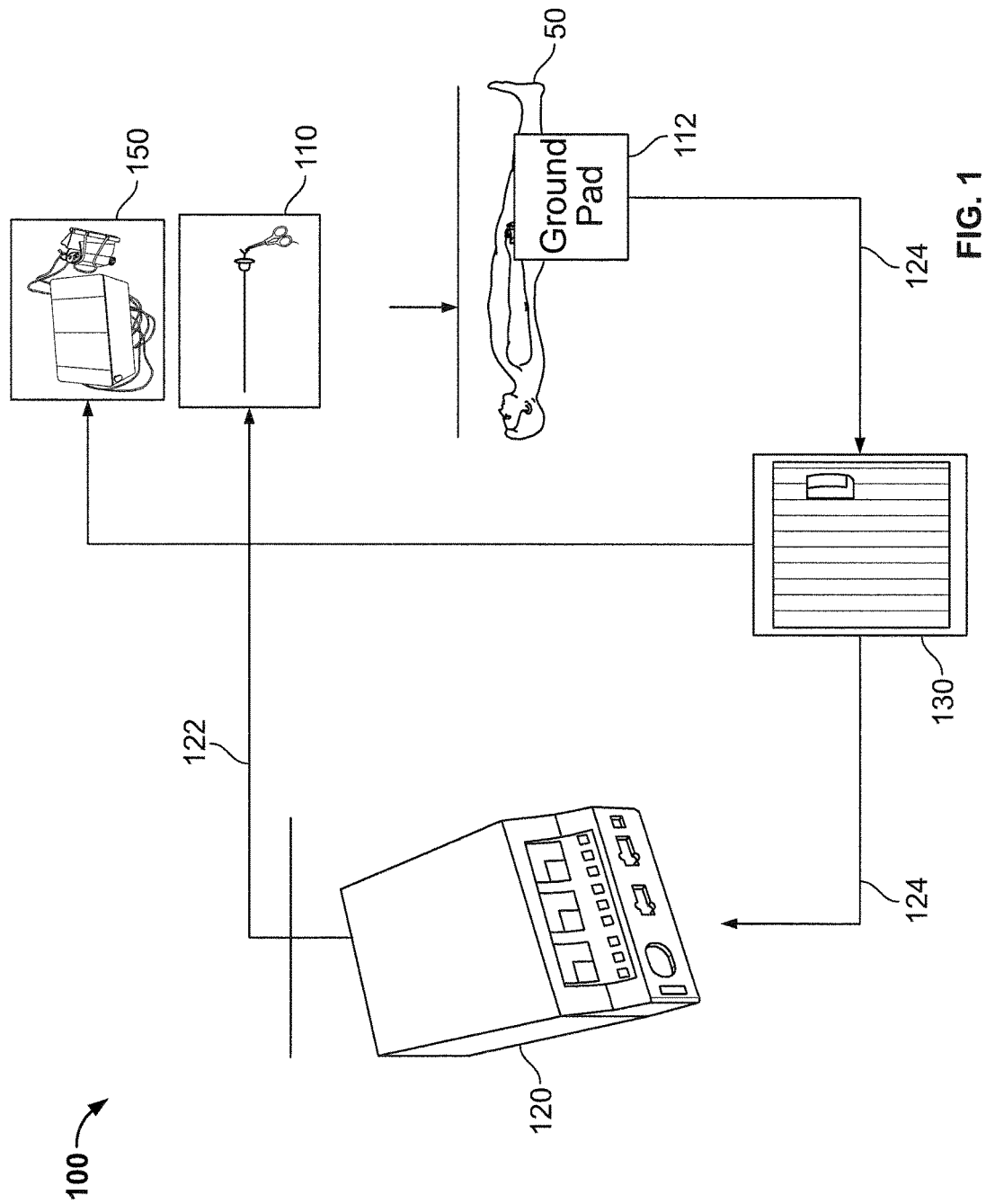
FIG. 1 is a diagram illustrating an exemplary surgery system for providing vibration feedback in accordance with aspects of the present invention.

Aspects of the present invention are directed to adding tactile feedback to electrocautery systems, and particularly, to monopolar electrocautery systems. In accordance with aspects of the present invention, vibrotactile feedback is provided to the surgeon when the cautery tool is in use (i.e., is on and in contact with tissue or another object (e.g. another tool)). Contact and/or active cautery may be determined, for example, by analyzing the signal returning to the generator through the ground pad (in monopolar electrocautery systems).

The exemplary devices disclosed herein may be particularly suitable as add-on components (e.g., as part of a kit) to supplement existing electrocautery systems that are used in the operating room. The exemplary devices can be used to increase the surgeon's awareness of the tool in open and minimally invasive (e.g., laparoscopic and/or robotic) surgery. This exemplary devices may be particularly important in laparoscopic surgery, in which the surgeon sees only a 2-dimensional view of the surgery and could benefit from additional cues of tool location and operation. Nonetheless, the exemplary devices described herein can be used for open, laparoscopic, and robotic surgery.

The exemplary systems and methods disclosed herein are particularly suitable for integration with and/or modification of robotic systems. For example, the system components described herein may be integrated with a robotic system having a remotely controlled robotic component. Suitable robotic systems may include a control station by which an operator may remotely operate the robotic component. The control station may include one or more control handles that are manipulated by the operator in operating the robotic component. In this configuration, the motions of the control handles may be transmitted to the robotic component, which will perform corresponding motions. An exemplary robotic system for use with the present invention is the DA VINCI Surgical System, provided by Intuitive Surgical, Inc.

The exemplary systems and methods disclosed herein may be particularly useful for use in conjunction with robotic surgical systems. As will be described below, the systems and methods disclosed herein may provide sensory feedback such as vibration feedback during the performance of a robot-assisted electrocautery operation, i.e., an electrocautery operation employing a robotic surgery system. As used herein, the term "vibration feedback" is intended to encompass tactile feedback as well as audio feedback. The vibration feedback may augment the surgeon's sensory experience during operations, thereby reducing cognitive load, and enabling a surgeon to perform robot-assisted surgeries more precisely, more quickly, and/or with greater ease and pleasure.

Although the systems and methods described below generally relate to electrocautery operations, it is contemplated that aspects of the present invention may be used with other operations in which the operator may not be able to visually identify whether a particular tool or device is in an active state (in use, powered, etc.). In other words, the present invention is not intended to be limited to electrocautery operations, and may be useful in operations (whether surgical or otherwise) other than electrocautery operations.

Referring now to the drawings, FIGS. 1-4B illustrate an exemplary surgery system 100 in accordance with aspects of the present invention. Surgery system 100 is operable to perform an electrocautery operation on a patient 50, while providing vibration feedback to an operation of system 100. As an overview, system 100 includes an electrocautery tool 110, a generator 120, a signal processing device 130, and a feedback device 150. Additional details of system 100 are described below.

Electrocautery tool 110 is an implement configured for performing an electrocautery action on patient 50. The electrocautery action may be, for example, a cutting operation for dissecting the tissue of patient 50, or a coagulation operation for the vasculature of patient 50. Exemplary electrocautery actions, and the procedures for performing those actions, will be known to those of ordinary skill in the art from the description herein.

Electrocautery tool 110 may be a bipolar electrocautery tool or a monopolar electrocautery tool. In an exemplary embodiment, electrocautery tool 110 is a monopolar electrocautery tool. As such, tool 110 includes a ground pad 112 in contact with patient 50 (e.g., coupled to the leg of patient 50). Ground pad 112 provides a return path for the current from tool 110 to exit the body of patient 50. Suitable electrocautery implements for use as electrocautery tool 110 will be known to those of ordinary skill in the art from the description herein.

Generator 120 is coupled to provide power to electrocautery tool 110. Generator generates the current for performing the electrocautery action and provides the current to electrocautery tool 110. Generator 120 provides current to tool 110 via one or more wires 122. Generator 120 also receives current back from electrocautery tool, e.g., from ground pad 112 via one or more wires 124. As shown in FIG. 1, wire 124 may pass through signal processing device 130, as will be discussed in detail below. Generator 120 may use the received current to control and/or regulate the current being provided to electrocautery tool 110. Suitable generators for use with electrocautery tool 110 will be known to those of ordinary skill in the art from the description herein.

Figure 2B:
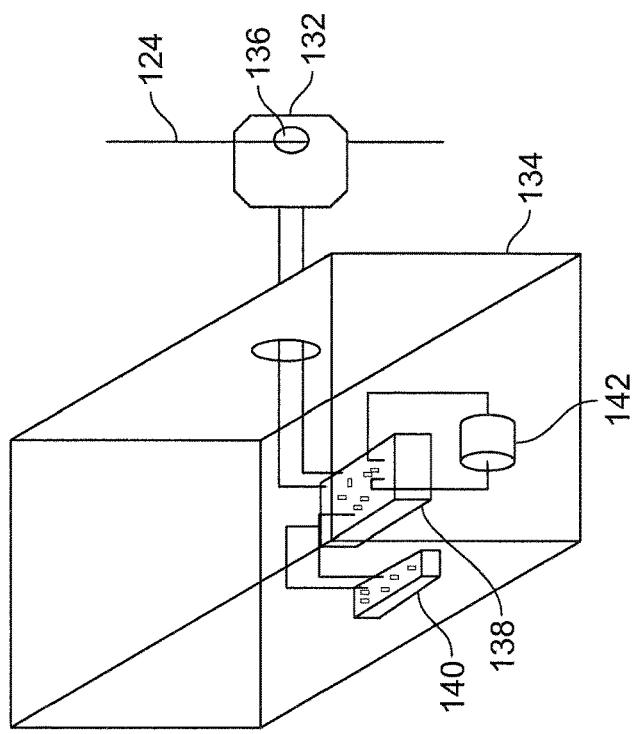
FIGS. 2A and 2B are an image and a diagram illustrating an exemplary signal processing device of the surgery system of FIG. 1.
Figure 2A:
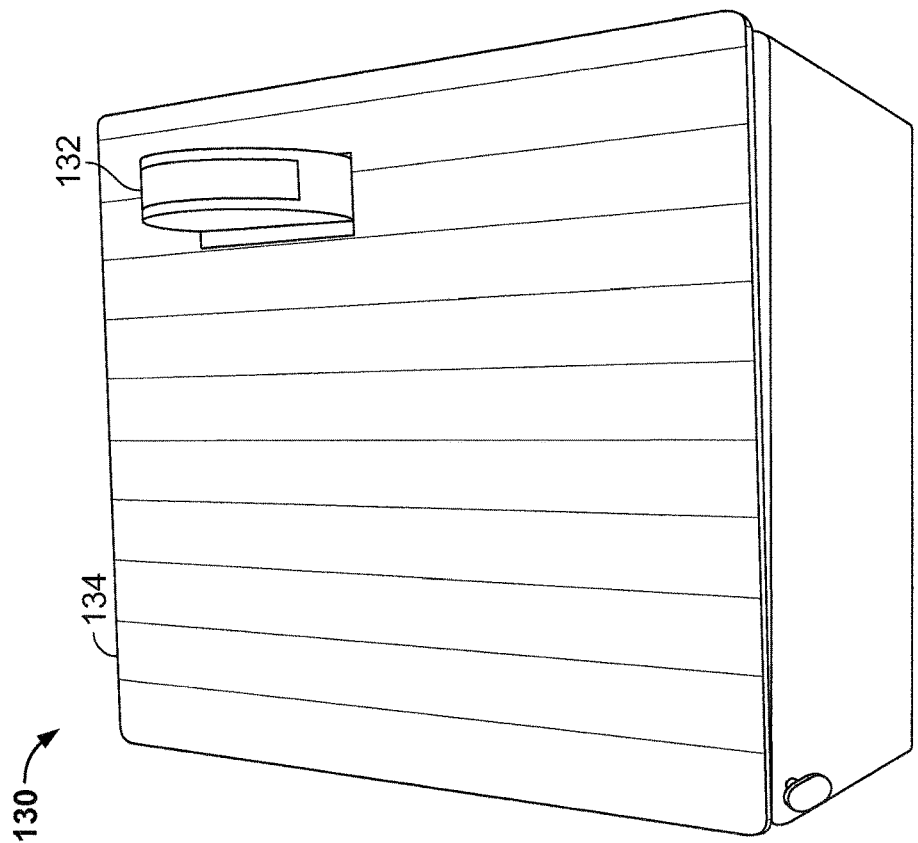

Signal processing device 130 processes signals that arise during operation of electrocautery tool 110. An exemplary signal processing device is illustrated in FIGS. 2A and 2B. Signal processing device 130 includes a current sensor 132. Current sensor 132 is coupled to electrocautery tool 110 to sense a current through electrocautery tool 110 indicative of the electrocautery action being performed with tool 110. Currently sensor 132 may be positioned within a case 134 defining the exterior of signal processing device 130, or may be positioning partially or entirely protruding from case 134. Alternatively, current sensor 132 could be embedded in a middle of case 134 of signal processing device 130, such that wire 124 passes through a middle of signal processing device 130, as shown in FIG. 1.

In an exemplary embodiment, current sensor 132 is inductively coupled to electrocautery tool 110, namely, current sensor 132 senses current through electrocautery tool 110 by induction. In this embodiment, current sensor 132 includes an opening 136 through its middle. The opening 136 may be formed through a middle of signal processing device 130 where current sensor 132 is positioned within case 134, or may be formed through a portion of current sensor 132 extending outward from case 134, as shown in FIGS. 2A and 2B. Prior to use, one or more of the wires between electrocautery tool 110 and generator 120 are passed through opening 136. In one embodiment, wire 124 from ground pad 112 to generator 120 is passed through opening 136. Then, during use of electrocautery tool 110, current sensor 132 detects the current through electrocautery tool 110 based on the change in flux through the opening of current sensor 132 caused by the current flowing through wire 124. In an exemplary embodiment, current sensor 132 is a 3.5 mH current sense inductor produced by Triad Magnetics of Perris, Calif., USA. It will be understood that current sensor 132 is not limited to any particular form or inductance value. Other suitable sensors for use as current sensor 132 will be known to one of ordinary skill in the art from the description herein.

Signal processing device 130 may desirably form part of a kit for modifying an existing surgery system having a conventional electrocautery tool 110 and generator 120. In this embodiment, current sensor 132 may be coupled to electrocautery tool 110 by simply passing wires 122 or 124 through opening 136 prior to connection to electrocautery tool 110 or ground pad 112, respectively. This may allow after-market provision of vibration feedback in existing surgery systems without the necessity of structurally modifying either electrocautery tool 110 or generator 120 to provide current sensing functionality.

Signal processing device 130 may desirably be coupled to wires 122 or 124 in an area of surgery system 100 that is outside of a sterile area. A surgery system may have a sterile area corresponding to an area in which an operation (e.g., an electrocautery operation) will be performed on patient 50. It may be desirable to position signal processing device 130 outside of this sterile area in order to avoid having to sterilize signal processing device 130.

Signal processing device 130 further includes a microcontroller 138. Microcontroller 138 processes the signals sensed by current sensor 132 to determine whether electrocautery tool 110 is in an active or a passive state. In particular, microcontroller 138 determines that electrocautery tool 110 is active when the current sensed by current sensor 132 exceeds a predetermined threshold. The threshold may be selected based on the operating parameters of electrocautery tool 110. For example, electrocautery tool 110 may receive a first, lower current flow when electrocautery is not occurring, and a second, higher current flow when electrocautery is occurring. In this example, the threshold may be selected so that the determination that tool 110 is active occurs only when a current flow sensed by current sensor 132 meets or exceeds the second, higher level.

When microcontroller 138 determines that electrocautery tool 110 is active, it is programmed to actuate feedback device 150 to provide feedback, as will be discussed below. Suitable processors for use as microcontroller 138 include, for example, the Arduino Nano. Other suitable processors will be known to one of ordinary skill in the art from the description herein.

In an exemplary embodiment, microcontroller 138 provides an activation signal to feedback device 150 only when (i) current sensor 132 senses current through electrocautery tool 110 indicative of electrocautery action, and (ii) microcontroller 138 has determined that electrocautery tool is in contact with tissue of patient 50. A Fourier transform and filtering may be used to analyze and process the frequency content of the signal sensed by current sensor 132 from electrocautery tool 110. Properties of the signal that may be analyzed to determine whether electrocautery tool 110 is in contact and cauterizing tissue include, for example: frequency content, voltage and current values, signal-to-noise ratio, how the signal changes during cauterization of tissue, and other properties known to those of ordinary skill in the art. Microcontroller 138 may be programmed to identify signals from the electrocautery tool indicative of tool contact and electrocautery action, and to provide the waveforms necessary to make the actuator of feedback device 150 vibrate during electrocauterization.

Signal processing device 130 further includes a transmitter 140. When microcontroller 138 determines from the sensed current that electrocautery tool 110 is active, microcontroller 138 transmits an activation signal to feedback device 150 by way of transmitter 140. The activation signal may include instructions of whether or not to actuate the actuator of feedback device 150, and may include information regarding the details of such actuation (e.g., time, amplitude, frequency, etc.), as discussed below. Desirably, microcontroller 138 processes the signals from current sensor 132 in real-time, and provides a real-time activation signal to feedback device 150 so that the vibration feedback is provided in real-time correspondence with the operation of electrocautery tool 110. As used herein, real-time refers to delays between the current sensing and vibration feedback of less than approximately 250 ms.

Microcontroller 138 may also be configured to control the amplitude or frequency of vibrations provided by feedback device 150. In an exemplary embodiment, microcontroller 138 generates an activation signal for transmission to feedback device 150 based on the amount of energy being supplied to the tissue of patent 50 with electrocautery tool 110. In other words, microcontroller 138 is configured to automatically adjust the frequency or amplitude of the vibration feedback provided by feedback device 150 based on the amount of energy provided by electrocautery tool 110. Such adjustments to the feedback may desirably provide the operator with additional information about the performance of the electrocautery action.

In an exemplary embodiment, transmitter 140 is a wireless transceiver. Suitable transceivers for use as transmitter 140 include, for example, XBee wireless communication modules, provided by Digi International of Minnetonka, Minn. United States. Other suitable wireless transceivers for use as transmitter 140 will be known to one of ordinary skill in the art from the description herein. Additionally, while transmitter 140 is described herein as a wireless transmitter, it will be understood that transmitter 140 may also take the form of a conventional wired transmitter.

Signal processing device 130 may further include a power source 142. Power source 142 provides power to the components of signal processing device 130, including microcontroller 138 and transmitter 140. While power source 142 is illustrated in FIG. 2B as being an internal power source (such as a battery), it will be understood that power source 142 may be external to signal processing device 130, and that in embodiments where system 100 is formed integrally with an electrocautery system, that signal processing device 130 may obtain power from the same source as the electrocautery system (e.g., from generator 120).

Figure 3:
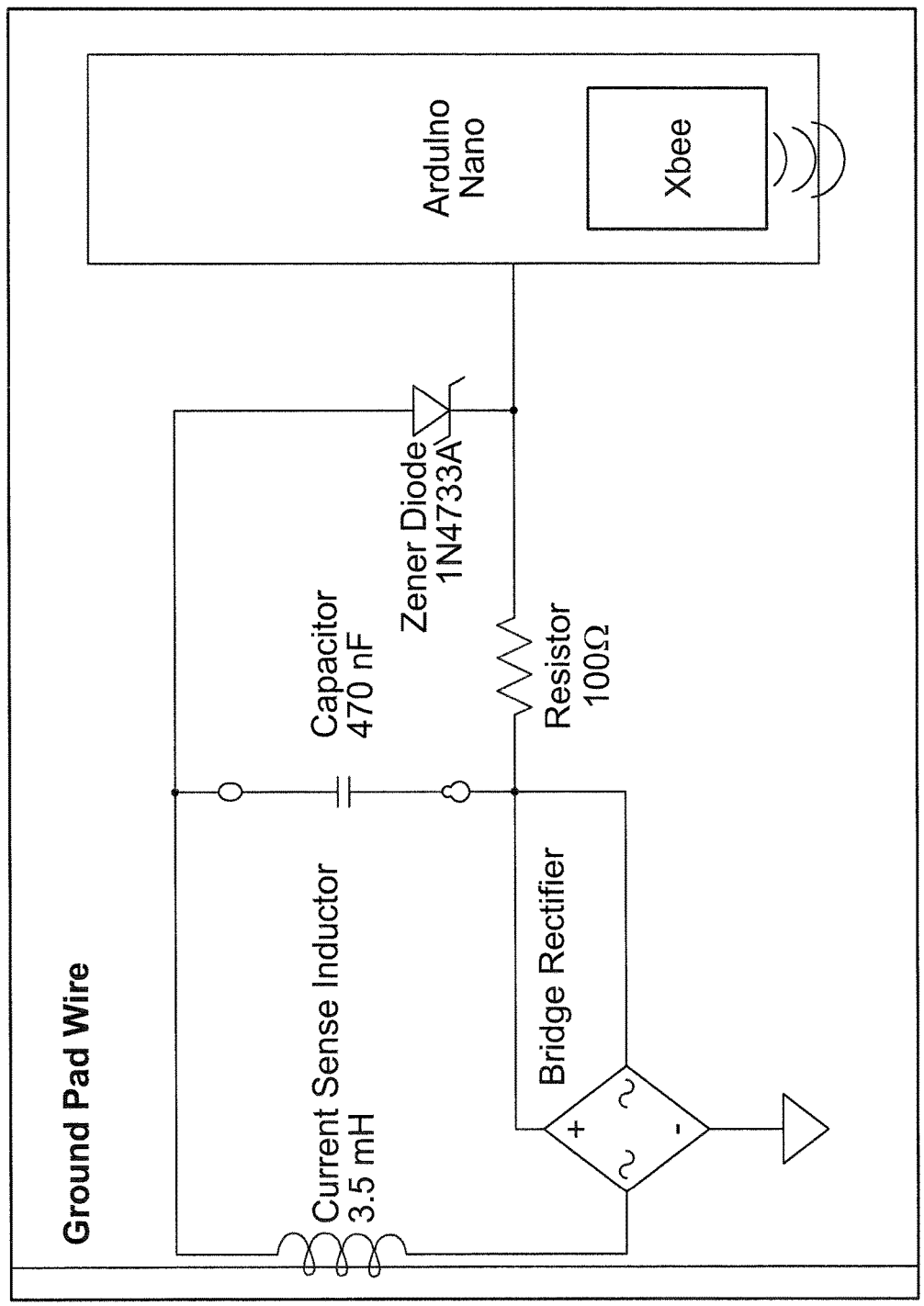
FIG. 3 is a schematic diagram illustrating an exemplary signal processing circuit of the signal processing device of FIGS. 2A and 2B.

FIG. 3 shows an exemplary circuit schematic for signal processing device 130 in accordance with aspects of the present invention. The schematic in FIG. 3 shows exemplary connections between current sensor 132, microcontroller 138, and transmitter 140. Such connections and component may preferably filter the signal sensed by current sensor 132 to make it suitable or safe for input to microcontroller 138. It will be understood that the particularized layout shown in FIG. 3 is provided for the purposes of illustration, and is not intended to be limiting of the layout of or components used in signal processing device 130.

While signal processing device 130 is illustrated as a stand-alone device in FIGS. 1 and 2A, it will be understood that the invention is not so limited. In other embodiments, signal processing device 130 may be incorporated into either electrocautery tool 110 or generator 120. In one exemplary embodiment, signal processing device 130 may be incorporated into the ground pad 112 of electrocautery tool 110, in order to more directly sense the current through electrocautery tool 110. In still another embodiment, signal processing device 130 may be configured to be coupled at one end directly to ground pad 112 of electrocautery tool 110, and at another end directly to generator 120. This may enable the omission of wire 124 from system 100, thereby simplifying the setup of system 100.

Feedback device 150 provides vibration feedback to the operator of electrocautery tool 110. An exemplary feedback device 150 is illustrated in FIGS. 4A and 4B. Feedback device 150 includes an actuator 152. Actuator 152 is in communication with microcontroller 138, which in turn receives information from current sensor 132, and is configured to provide vibrations to the operator of electrocautery tool 110 when current sensor 132 senses current through electrocautery tool 110 indicative of electrocautery action being performed. Actuator 152 may provide vibration feedback having a frequency, for example, of anywhere between 50-250 Hz. Actuator 152 may be positioned within a case 154 defining the exterior of feedback device 150, or may be position on the exterior of case 154 in order to directly provide vibrations to the operator without any intervening structure.

In an exemplary embodiment, actuator 152 is configured to be attached to the operator of electrocautery tool 110. In this embodiment, actuator 152 may include an attachment band 156 configured to encircle one of the user's limbs (e.g., an armband). The positioning of the actuator on the body of the operator may be selected based on the most effective provision of vibration feedback and/or based on the operator's preferences. Alternatively, actuator 152 may be configured to be attached to the operator's clothes, or to electrocautery tool 110. Attachment of actuator 152 to electrocautery tool 110 may desirably provide more direct vibration feedback to the operator during the electrocautery process.

In an exemplary embodiment, actuator 152 is the 312-201 vibration motor provided by Precision Microdrives of London, UK. Other suitable actuators will be known to one of ordinary skill in the art from the description herein.

As set forth above, the term "vibration feedback" is used herein to encompass audio feedback. Accordingly, while actuator 152 is described above as providing physical vibrations to the operator of surgery system 100, it will be understood that actuator 152 may also provide audio signals to the operator. Alternatively, actuator 152 may exclusively provide audio signals (as opposed to other high frequency vibrations) to the operator of surgery system 100. For example, actuator 152 may be a speaker, and may be so as to provide audio in place of vibrations during an operation. Additionally, feedback device 150 may provide other additional forms of feedback (e.g., visual feedback) using one or more conventional components, as would be understood by one of ordinary skill in the art from the description herein.

Feedback device 150 may desirably form part of a kit for modifying an existing surgery system having a conventional electrocautery tool 110 and generator 120. In an exemplary embodiment, the existing surgery system is a robotic surgery system having an armature configured to manipulate electrocautery tool 110 and a control station, positioned remote from the armature, having a control handle configured to operate the armature. Suitable robotic surgery systems having this or other configurations will be known to those of ordinary skill in the art from the description herein.

In this embodiment, actuator 152 may be coupled to provide vibration to the control handle manipulated by the operator. This may allow after-market provision of vibration feedback in existing robotic surgery systems without the necessity of structurally modifying the control handle or other components of the system to provide s vibration feedback functionality.

In another exemplary embodiment, the operator of surgery system 100 may be configured to actuate generator 120 to supply current through electrocautery tool 110 by actuating a pedal with the operator's foot. In this embodiment, actuator 152 may be attached directly to the user's foot, to assist the user in associating the vibration feedback provided by actuator 152 with the operator's control over the current flowing through electrocautery tool 110.

Feedback device 150 further includes a microcontroller 158. Microcontroller 158 processes the signals received from signal processing device 130, and actuates actuator 152 according to those signals. Where the signals received from signal processing device 130 include characteristics for operation actuator 152 (e.g., amplitude, frequency, etc.), microcontroller 158 actuates actuator 152 in accordance with those characteristics.

Feedback device 150 further includes a receiver 160. When microcontroller 138 transmits an activation signal to feedback device 150 by way of transmitter 140, receiver 160 receives the signal and provides the signal to microcontroller 158. In an exemplary embodiment, receiver 160 is a wireless transceiver substantially as described above with respect to transmitter 140. Receiver 160 may be wireless or may take the form of a conventional wired receiver depending on the configuration of transmitter 140.

Feedback device 150 may further include a power source 162. Power source 162 provides power to the components of feedback device 150, including actuator 152, microcontroller 158, and receiver 160. While power source 162 is illustrated in FIG. 4B as being an internal power source (such as a battery), it will be understood that power source 162 may be external to feedback device 150, as described above with respect to power source 142.

Feedback device 150 may further include an adjustment device (not shown). The adjustment device desirably enables the operator to manually adjust a frequency or amplitude of the vibrations being provided by actuator 152. Such adjustment may desirably enable the operator to tune the characteristics of the vibration feedback to a level they find most comfortable or effective. In an exemplary embodiment, the adjustment device may be a dial, knob, or other conventional structure.

Figure 5:
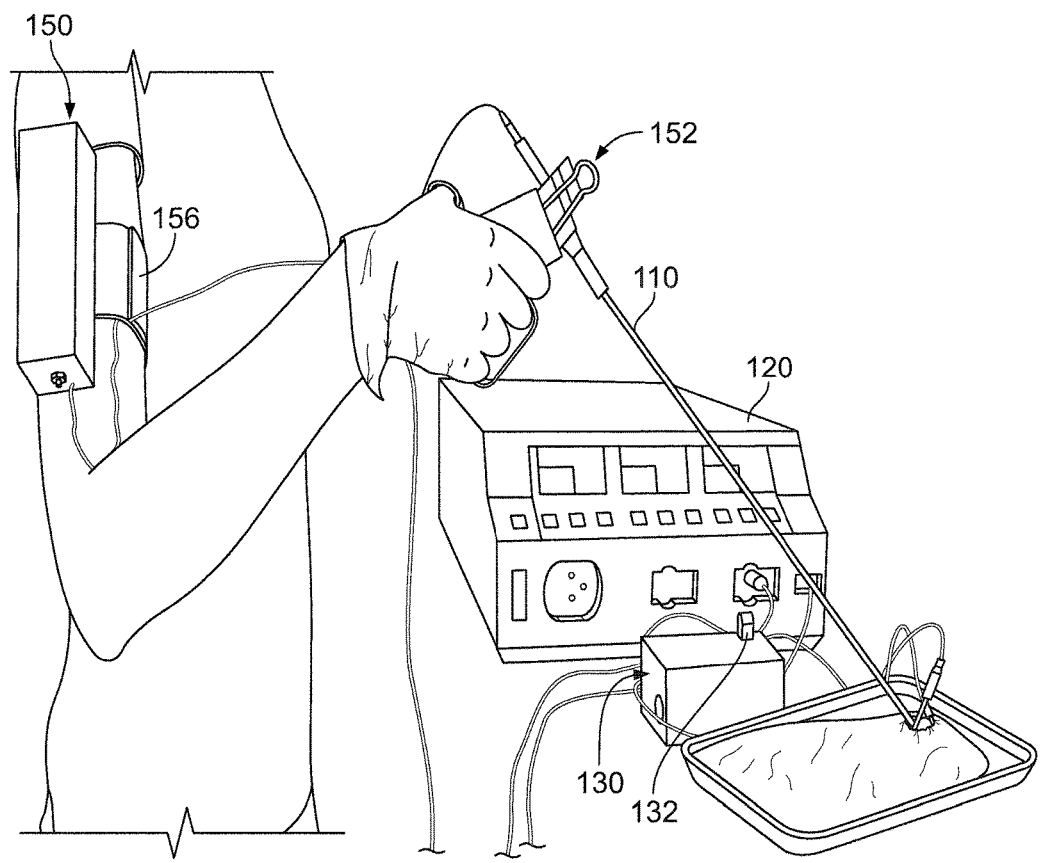
FIG. 5 is an image illustrating an exemplary surgical procedure in accordance with aspects of the present invention.

FIG. 5 illustrates an exemplary surgical procedure performed with surgery system 100 in accordance with aspects of the present invention. As shown in FIG. 5, the operator of system 100 grasps electrocautery tool 110, and physically manipulates tool 110 during the procedure to perform an electrocautery action. A wire extending between generator 120 and tool 110 passes through an opening formed at the periphery of signal processing device 130, which enables current sensor 132 to detect current flowing through electrocautery tool 110. Upon sensing current, signal processing device 130 wireless transmits in real-time an activation signal to feedback device 150, which is attached to the arm of the operator using attachment band 156. Feedback device 150 then actuates actuator 152, which is coupled to electrocautery tool 110. The actuation of actuator 152 provides vibration feedback to the operator, which reinforces to the operator that an electrocautery action is being performed with tool 110. It will be understood by one of ordinary skill in the art that the positioning of the various components of surgery system 100 shown in FIG. 5 is done for the purposes of illustration, and is not intended to be limiting.

Figure 6:
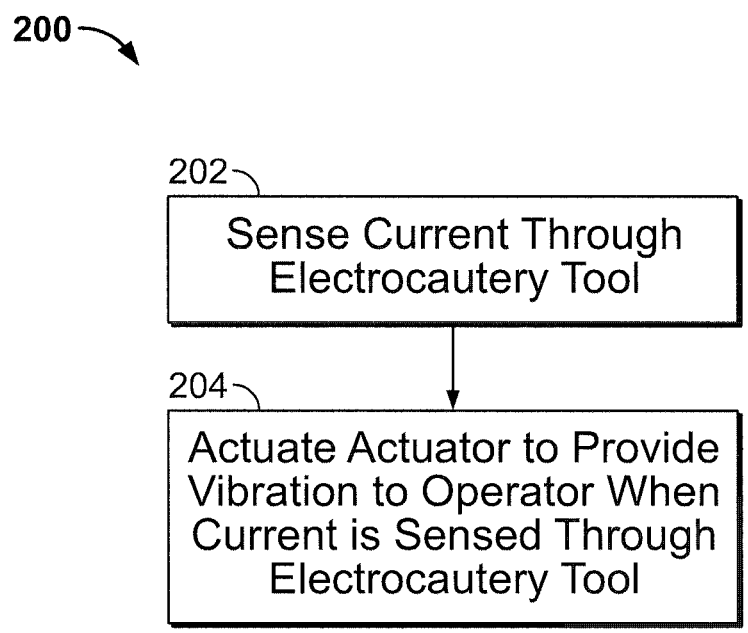
FIG. 6 is a flowchart illustrating an exemplary method for providing vibration feedback in accordance with aspects of the present invention.

FIG. 6 is a flowchart illustrating an exemplary method 200 for providing vibration feedback during electrocauterization in accordance with aspects of the present invention. As an overview, method 200 includes sensing current through an electrocautery tool and actuating an actuator to provide the vibration feedback. For the purposes of illustration, the steps of method 200 are described herein with respect to the components of system 100. Additional details of method 200 are described below.

In step 202, a current is sensed. In an exemplary embodiment, current sensor 132 senses a current flowing through electrocautery tool 110 indicative of an electrocautery action being performed with tool 110. The electrocautery action may be, for example, a cutting operation for dissecting the tissue of patient 50, or a coagulation operation for the vasculature of patient 50.

In a further exemplary embodiment, current sensor 132 senses current flowing through electrocautery tool 110 by induction. Where electrocautery tool 110 is a monopolar electrocautery tool, the wire 124 from ground pad 112 to generator 120 may be passed through opening 136 of current sensor 132 to enable the inductive sensing of current flow through tool 110.

In step 204, an actuator is actuated. In an exemplary embodiment, actuator 152 is actuated to provide a vibration to the operator of electrocautery tool 110. When microcontroller 138 determines that an electrocautery action is being performed based on the current flowing through electrocautery tool 110 sensed by current sensor 132, it sends an activation signal to feedback device 150 to actuate actuator 152. Microcontroller 138 may be programmed to send the signal only when (i) current sensor 132 senses current through electrocautery tool 110 indicative of electrocautery action, and (ii) microcontroller 138 has determined that electrocautery tool is in contact with tissue of patient 50, as set forth above.

Method 200 may also include the step of automatically adjusting the amplitude and/or frequency of vibration provided by actuator 152. In an exemplary embodiment, microcontroller 138 is configured to automatically adjust the frequency or amplitude of the vibration feedback provided by feedback device 150 based on the amount of energy provided by electrocautery tool 110. Alternatively or additionally, the operator of surgery system 100 may manually adjust the amplitude or frequency of the vibration provided by actuator 152 using an adjustment device.

The disclosed systems and methods differ from conventional feedback systems for at least the following reasons:

The disclosed systems and methods provide add-on components for existing open, laparoscopic, and/or robotic electrocautery tools, and do not necessarily require the production of an entirely new electrocautery system. However, it will be understood by one of ordinary skill in the art that the disclosed systems and methods may be integrally incorporated into a new electrocautery system in accordance with aspects of the present invention.

The disclosed systems and methods work with monopolar electrocautery. However, it will be understood by one of ordinary skill in the art that the disclosed systems and methods may be used with bipolar electrocautery systems in accordance with aspects of the present invention.

The disclosed systems and methods provide vibrotactile feedback based on whether the surgeon is cauterizing tissue. This enables the surgeon to know when current is being applied to the tissue, which may otherwise not be visible to the surgeon (e.g., if out of view of the surgeon or a camera).

Although the invention is illustrated and described herein with reference to specific embodiments, the invention is not intended to be limited to the details shown.

Rather, various modifications may be made in the details within the scope and range of equivalents of the claims and without departing from the invention.

What is claimed:

1. A method for providing vibration feedback during electrocauterization, comprising the steps of:
    sensing a current through an electrocautery tool by induction indicative of an electrocautery action being performed with the tool; and
    actuating an actuator to provide a vibration to an operator of the electrocautery tool when the current sensor senses the current through the electrocautery tool indicative of the electrocautery action.

2. The method of claim 1, wherein the electrocautery action comprises at least one of a cutting operation or a coagulation operation.

3. The method of claim 1, wherein the sensing step comprises sensing the current passing from a ground pad of a monopolar electrocautery tool.

4. The method of claim 1, wherein the actuating step comprises actuating the actuator to provide a vibration to the operator of the electrocautery tool only when (i) the current sensor senses the current through the electrocautery tool indicative of the electrocautery action and (ii) the electrocautery tool is in contact with tissue.

5. The method of claim 1, further comprising the step of:
    automatically adjusting a frequency or amplitude of the vibration provided to the operator based on an amount of energy being supplied to tissue with the electrocautery tool.

\* \* \* \* \*